Figure 1:
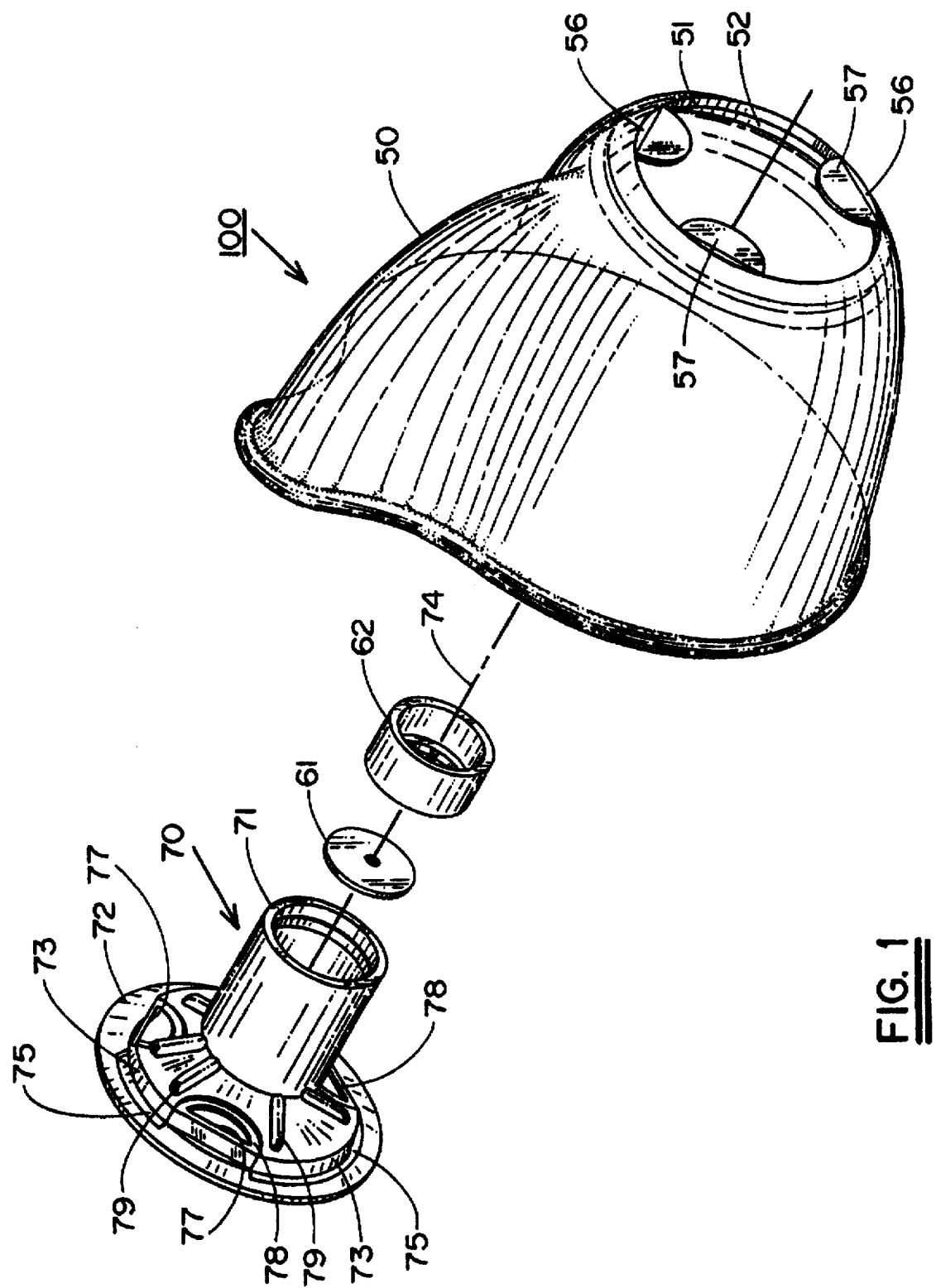

United States Patent [19]

Richards et al.

[11] Patent Number: 5,765,553
[45] Date of Patent: Jun. 16, 1998

[54] AEROSOL MEDICATION DELIVERY FACEMASK ADAPTER

[75] Inventors: Frederick M. Richards, Clinton; Stephen J. Scheuermann, Oneida, both of N.Y.

[73] Assignee: Diemolding Corporation, Canastota, N.Y.

[21] Appl. No.: 757,833

[22] Filed: Nov. 27, 1996

[51] Int. Cl.$^6$ ................................................ A61M 11/00
[52] U.S. Cl. ............................ 128/203.29; 128/203.12; 128/206.21; 128/200.14
[58] Field of Search ...................... 128/206.21, 203.15, 128/203.29, 200.14, 200.22, 200.23, 203.12, 912

[56] References Cited

U.S. PATENT DOCUMENTS

| | | |
|---|---|---|
| 831,623 | 9/1906 | Murphy . |
| 1,084,182 | 1/1914 | Von Ach . |
| 1,671,010 | 5/1928 | Braecklein . |
| 1,671,011 | 5/1928 | Braecklein . |
| 1,683,686 | 9/1928 | McMillan . |
| 2,788,784 | 4/1957 | Birch et al. .................... 128/201 |
| 3,027,896 | 4/1962 | Newton .......................... 128/195 |
| 3,490,452 | 1/1970 | Greenfield ....................... 128/196 |
| 3,815,597 | 6/1974 | Goettelman ...................... 128/196 |
| 4,484,577 | 11/1984 | Sachner et al. ................. 128/203.28 |
| 4,582,054 | 4/1986 | Eerrer ............................ 128/200.23 |
| 4,809,692 | 3/1989 | Nowacki et al. ................. 128/206.24 |
| 4,832,015 | 5/1989 | Nowacki et al. ................. 128/205.23 |
| 4,865,027 | 9/1989 | Laanen et al. ................... 128/200.21 |
| 4,938,209 | 7/1990 | Fry .............................. 128/200.21 |
| 5,012,803 | 5/1991 | Eoley et al. .................... 128/200.23 |
| 5,012,804 | 5/1991 | Eoley et al. .................... 128/200.23 |
| 5,318,016 | 6/1994 | Mecikalski ...................... 128/203.12 |
| 5,357,945 | 10/1994 | Messina ......................... 128/200.14 |
| 5,385,140 | 1/1995 | Smith ............................ 128/203.29 |
| 5,427,089 | 6/1995 | Kraemer ......................... 128/200.23 |

FOREIGN PATENT DOCUMENTS 2631833  12/1989  France ................. 129/203.29

Primary Examiner—Aaron J. Lewis
Assistant Examiner—William J. Deane, Jr.
Attorney, Agent, or Firm—August E. Roehrig, Jr.

[57] ABSTRACT

A non-rebreathing facemask removably securable onto a connector which is attachable directly to an aerosol medication system, illustrated for example as an aerosol cloud enchancer for use in respiratory therapy, or an oxygen delivery system. The connector to which the facemask is secured functions in cooperation with the facemask to provide a valving system for discharging a patient's expiratory air outside of the medication or oxygen delivery system, while permitting the patient to smoothly inhale inspiratory air.

9 Claims, 2 Drawing Sheets

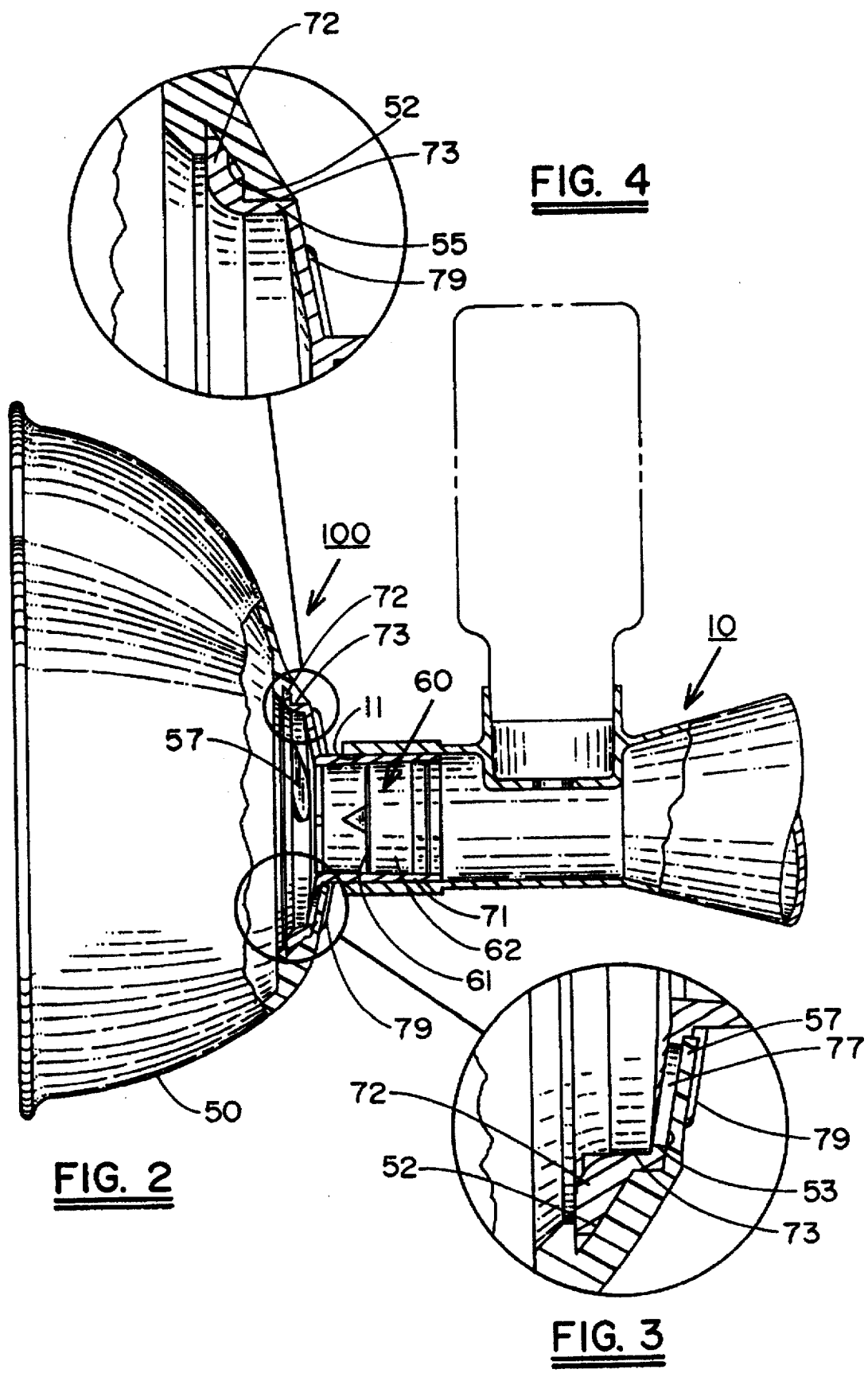

AEROSOL MEDICATION DELIVERY FACEMASK ADAPTER

BACKGROUND OF THE INVENTION

This invention relates in general to respiratory therapy devices and, in particular, to a facemask which may be advantageously adapted for use in aerosol medication or oxygen delivery.

More specifically, but without restriction to the particular embodiment and/or use which is shown and described herein for purposes of illustration, this invention relates to a facemask which is adapted to used in aerosol medication or oxygen delivery by persons, for example pediatric patients, who are not able to utilize a mouthpiece for their treatments.

Persons who require the use of medication to enhance or facilitate their ability to breathe, can take such medication in the form of pills, intravenously or through the use of an inhalant. Inhalation therapy provides a convenient method of delivering the medication to a patient which can promptly and effectively treat swollen membranes and bronchi. However, because of the physical condition of some patients, due to their age or infirmity, their use of an inhalant has been difficult because of their inability to properly hold or use a mouthpiece.

To overcome the problems some patients encounter when attempting to utilize a mouthpiece, facemasks have been developed which seal against a patient's face covering the patient's mouth and nose. While various facemasks have been developed, such as those disclosed in the Information Disclosure Statement filed by the present inventors concurrently with their application, these prior devices have alleviated the problem of a patient's inability to hold a mouthpiece, but have shortcomings which the present invention has resolved.

SUMMARY OF THE INVENTION

It is, therefore, an object of this invention to improve face masks for use in inhalation therapy.

Another object of this invention is to connect the facemask to the body of an aerosol cloud enhancer without affecting the performance characteristics of a metered dose inhaler with which the facemask is utilized.

A further object of this invention is to prevent a patient's expiratory air from passing into the body of the respiratory therapy aerosol medication system, but allow inspiratory air to pass smoothly therethrough into the facemask.

Still another object of this invention is to preclude any interference with the usage monitoring systems of the respiratory therapy device, such as a whistle to monitor proper breathing, when in use.

These and other objects are attained in accordance with the present invention wherein there is provided a non-rebreathing facemask removably securable onto a connector which is attachable directly to the body of an aerosol medication or oxygen delivery system for use in respiratory therapy. The connector to which the facemask is secured functions in cooperation with the facemask to provide a valving system for discharging a patient's expiratory air outside of the aerosol medication delivery system, for example an aerosol cloud enhancer, while permitting the patient to smoothly inhale inspiratory air.

DESCRIPTION OF THE DRAWING

Further objects of this invention, together with additional features contributing thereto and advantages accruing therefrom, will be apparent from the following description of a preferred embodiment of the invention which is shown in the accompanying drawings with like reference numerals indicating corresponding parts throughout and which is to be read in conjunction with the following drawings, wherein:

FIG. 1 is an exploded perspective view of the invention to better illustrate the parts thereof;

FIG. 2 is a side profile view of the invention, with parts broken away to better illustrate the internal construction thereof, connected to an aerosol cloud enhancer; and

FIGS. 3 and 4 are enlarged views of a portion of FIG. 2, as shown by the interconnected balloons.

DESCRIPTION OF A PREFERRED EMBODIMENT

Referring now to the drawings, there is shown in FIG. 1 a facemask 100 for use with an aerosol cloud enhancer, a portion of which is shown in FIG. 2. A mask portion, formed of a soft elastomeric material such as natural, translucent silicone rubber is shaped to conform to a face for covering the nose and mouth when in use. An opening 51 is formed in the mask portion 50 for receiving a connector 70 upon which the mask portion is mounted. The connector 70 has an outwardly extending end portion 71 which, in use, is received within an opening 11 of the aerosol cloud enhancer 10. To this end the diameter of the end portion 71 is sized to be compatible with 22 mm fittings.

The connector 70 is sealed against the inner surface of the opening 51 in the face mask portion 50 to form the face mask valving system. To this end the interior of the face mask portion 50 adjacent to the opening 51 is formed with a stepped groove 52 extending circumferentialy about the interior of the opening for receiving a lip 72 formed on the outer diameter of the connector, when the connector is positioned in the opening 51. A shoulder portion 73 of the connector extends outwardly parallel to the connectors longitudinal axis 74, and is received against a complementary ridge 53 formed on the interior of the face mask portion. Three equal sized and equi-spaced protrusions 55 are formed at the leading edge of the ridge 53 to engage complementary recesses 75 formed in the connector to assist in properly positioning and sealing the connector in the opening 51.

To facilitate the passage of expiratory air out from the facemask, the ridge 53 of the facemask portion is undercut 56 at each position adjacent to the flatted portions 76 of the connector 70, with the protrusions 55 spaced therebetween. Three flaps 57 extend inwardly from the inner peripheral edge of the opening 51 toward the longitudinal axis 74 to form one-way valves through which expiratory air may be freely passed from the facemask. To this end complementary openings 77 are formed in the connector and positioned in alignment with the flaps 57. The openings 77 are each formed with a step portion 78 such that when a patient inhales, the flaps 57 are drawn down tightly to cover the openings 77 preventing the passage of inspiratory air through the flap valves. Adjacent to each side of the openings 77 is a guard 79 to prevent inadvertent interference by a patient with the operation of the flap valves.

Positioned within the outwardly extending end portion 71 of the connector is a one-way diaphragm valve 60 through which a patient draws inspiratory air, but which prevents the passage of expiratory air. As inspiratory air is drawn in by the patient, a diaphragm 61 moves away from a guard 62 and allows air to be drawn into the mask. When the patient exhales, however, the diaphragm 61 is forced against the guard 62, sealing the passage. In this manner inspiratory air is freely drawn into the facemask 100 through the aerosol cloud enhancer 10 while expiratory air is freely passed from the mask without discharge through the cloud chamber.

While this invention has been described in the specification and illustrated in the drawings with reference to a preferred embodiment utilized with an aerosol cloud enhancer, the structure of which has been disclosed herein, it will be understood by those skilled in the art to which this invention pertains that various changes may be made and equivalents may be substituted for elements of the invention without departing from the scope of the claims. For example, different sizes of facemasks, for use with infants, children and adults may be mounted on the same connector for coupling the facemask to a respiratory therapy device. In addition, the facemask can be used with various types of aerosol medication delivery systems. Therefore, it is intended that the invention not be limited to the particular embodiment disclosed in the specification and shown in the drawings as the best mode presently known by the inventor (s) for carrying out this invention, nor confined to the details set forth, but that the invention will include all embodiments, modifications and changes as may come within the scope of the following claims:

What is claimed is:

1. A facemask for use with a respiratory therapy device or oxygen delivery system comprising:

a mask portion adapted to conform to a portion of a face of a user to cover a nose and mouth of a user;

said mask portion having an opening therein for receiving therethrough a connector for coupling said facemask to a respiratory therapy device or oxygen delivery system;

a connector adapted to be received and retained in said opening in said facemask for coupling said facemask to a respiratory therapy device or oxygen delivery system;

said connector having a central portion extending outwardly therefrom for engaging and coupling thereto a respiratory therapy device or oxygen delivery system;

said central portion of said connector having carried therein a one-way inspiratory air valve through which inspiratory air may be drawn into said mask portion from a respiratory therapy device or oxygen delivery system when coupled thereto;

said connector having at least one opening formed therein through which expiratory air may be passed from said facemask without passing into a respiratory therapy device or oxygen delivery system when coupled thereto; and said mask portion having at least one one-way valve formed thereby through which expiratory air may be passed to said expiratory air opening formed in said connector.

2. The facemask of claim 1 wherein said opening formed in said connector through which expiratory air may be passed, and said one-way valve formed by said mask portion through which expiratory air may be passed comprise a one-way flap valve.

3. The facemask of claim 2 wherein said one-way inspiratory air valve carried in said central portion of said connector comprises a one-way diaphragm valve.

4. The facemask of claim 2 wherein said expiratory air opening in said connector is stepped to facilitate the sealing of the flap of said mask portion thereagainst upon inhalation of a user.

5. The facemask of claim 1 further including means formed within said opening of said mask portion for retaining said connector.

6. The facemask of claim 1 wherein said one-way valve through which expiratory air is passed to said expiratory air opening formed in said connector is positioned adjacent to a users mouth.

7. A connector adapted to be received and retained in an opening in a facemask for coupling the facemask to a respiratory therapy device or oxygen delivery system comprising:

a facemask connector having a central portion extending outwardly therefrom for engagement with and coupling to a respiratory therapy device or oxygen delivery system, and a facemask connecting portion for engagement with and coupling to a facemask;

said central portion of said connector including a one-way inspiratory air valve through which inspiratory air may be drawn through said connector into a facemask from a respiratory therapy device or oxygen delivery system when coupled thereto; and said facemask connecting portion forming a portion of at least one expiratory air valve through which expiratory air may be passed when said connector is coupled to the facemask without passing the expiratory air into the respiratory therapy device or oxygen delivery system when coupled thereto.

8. The connector of claim 7 wherein said portion of at least one expiratory air valve comprises at least one valve seat formed in said facemask connecting portion for engagement with a one-way flapper valve carried by the facemask.

9. The connector of claim 8 wherein said valve seat formed in said facemask connecting portion is formed in a position adjacent to a user's mouth.

* * * * *